United States Patent [19]

Mayer et al.

[11] 4,065,568
[45] Dec. 27, 1977

[54] 3-CARBO(LOWER ALKOXY)HYDRAZINOINDAZOLES

[75] Inventors: Karl Heinrich Mayer, Opladen; Friedrich Hoffmeister; Wolfgang Wuttke, both of Wuppertal, all of Germany

[73] Assignee: Bayer Aktiengesellschaft, Germany

[21] Appl. No.: 634,913

[22] Filed: Nov. 24, 1975

[30] Foreign Application Priority Data

Dec. 13, 1974 Germany .............................. 2458966

[51] Int. Cl.$^2$ .................. A61K 31/415; C07D 231/56
[52] U.S. Cl. ................................. 424/273 P; 548/359
[58] Field of Search ..................... 260/310 C; 424/273

[56] References Cited

PUBLICATIONS

Liebigs "Ann. Chem." 305, pp. 289–370 (1899) & 747, pp. 1–13 (1971).

Primary Examiner—Donald B. Moyer
Attorney, Agent, or Firm—Jacobs & Jacobs

[57] ABSTRACT

3-Hydrazinoindazoles acylated with a carbo(lower alkoxy) group in the 3-position and further being optionally substituted in one or more of the 4-, 5-, 6- and/or 7-positions are analgesic, anti-inflammatory and antipyretic agents. The compounds, of which 3-carbomethoxyhydrazino-6-chloroindazole is a typical embodiment, are prepared through treatment of the appropriate 3-hydrazinoindazole with a derivative of carbonic acid.

12 Claims, No Drawings

3-CARBO(LOWER ALKOXY)HYDRAZINOINDAZOLES

DETAILED DESCRIPTION

The present invention pertains to new 3-carbo(lower alkoxy)hydrazinoindazole derivatives, processes for their preparation and use, and to pharmaceutical compositions for achieving analgesic, anti-inflammatory and antipyretic effects.

Certain 3-aminoindazoles have been described in German Published Specification No. 1,280,878 as analgesics and antipyretics, 3-amino-5-trifluoromethylindazole being particularly singled out as having especially advantageous therapeutic properties. 3-Aminoindazoles are also known in dyestuff chemistry where they are useful as starting materials. (See German Published Specification No. 1,149,839).

The present invention pertains to 3-carbo(lower alkoxy)hydrazinoindazoles of the formula:

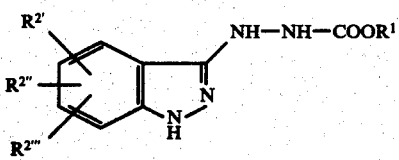

wherein
$R^1$ is lower alkyl; and each of $R^{2'}$, $R^{2''}$ and $R^{2'''}$ is selected, independently of the others, from the group consisting of hydrogen, lower alkyl, lower alkoxy, nitro, amino, lower alkylamino, di(lower alkyl)amino, lower alkanoylamino, carbo(lower alkoxy)amino, halo, trifluoromethyl, cyano and carbo(lower alkoxy), and the pharmaceutically acceptable nontoxic salts thereof.

The foregoing compounds of Formula I and their salts demonstrate valuable action on the central nervous system, in particular excellent analgesic, antipyretic and anti-inflammatory properties. Surprisingly, these 3-carbo-(lower alkoxy)hydrazinoindazoles are better tolerated and exert substantially greater analgesic, antipyretic and antiphloistic (anti-edematous) action than known aminoindazoles such as 3-amino-5-trifluoromethylindazole, which might be deemed chemically to be the closest related compound.

In the context of the present specification and claims, the term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

Lower alkanoyl denotes the residue of a straight or branched alkanoic acid of from 1 to 6 carbon atoms such as formyl, acetyl, propionyl, butyryl, isobutyryl, valeroyl, isovaleroyl, pivaloyl and the like.

The term halo denotes the monovalent substituents fluoro, chloro, bromo and iodo. As a substituent, chloro, fluoro or bromo, particularly chloro, is preferred. As a reactive nucleofugic group as in alkylating or acylating reagents, chloro or bromo is preferred.

In a first preferred embodiment, the invention pertains to the compounds depicted by Formula I wherein each of $R^{2'}$, $R^{2''}$ and $R^{2'''}$ is selected, independently of the others, from the group consisting of hydrogen, chloro, trifluoromethyl, nitro, amino, cyano, lower alkyl or carbo(lower alkoxy)amino.

A further embodiment pertains to compounds wherein each of $R^{2'}$ and $R^{2'''}$ is hydrogen and $R^{2''}$ is chloro or trifluoromethyl. Within this embodiment a preferred class entails those compounds wherein $R^{2''}$ is chloro or trifluoromethyl in the 5- or 6-position of the indazole ring.

A further embodiment pertains to compounds wherein $R^{2''}$ is chloro in the 6-position of the indazole ring.

A further embodiment pertains to compounds wherein $R^1$ is methyl, ethyl, propyl, isopropyl or butyl.

The compounds of the present invention can be prepared by treating a 3-hydrazinoindazole of the formula:

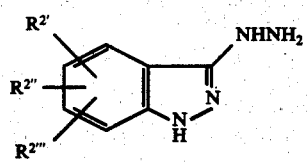

with a halocarbonic acid lower alkyl ester or di(lower alkyl)-pyrocarbonate.

The following typifies the foregoing reaction:

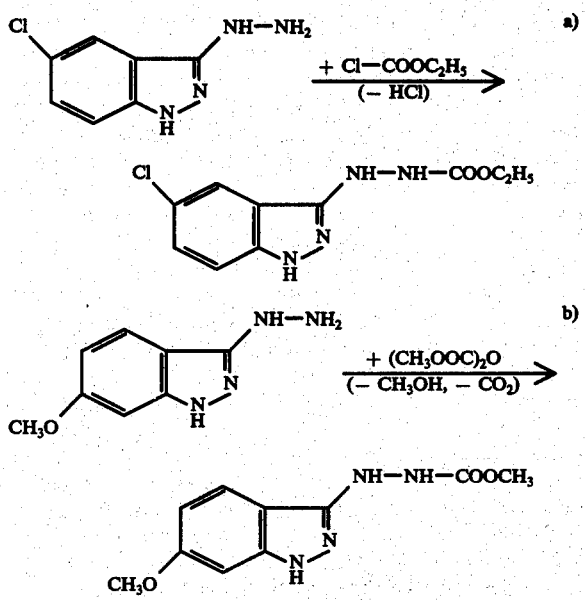

The 3-hydrazinoindazoles of Formula II used as starting materials are known or can be readily prepared according to known processes, see e.g. J. chem. Soc. (London) 1963, 5901. The following are typical examples: 3-hydrazinoindazole, 3-hydrazino-5-methylindazole, 3-hydrazino-6-n-butylindazole, 3-hydrazino-5,7-dimethylindazole, 3-hydrazino-5-methoxyindazole, 3-hydrazino-6-ethoxyindazole, 3-hydrazino-5,6-bis-methoxyindazole, 3-hydrazino-5-nitroindazole, 3-hydrazino-5,7-dinitroindazole, 3-hydrazino-5-dimethylaminoindazole, 3-hydrazino-5-acetylaminoindazole, 3-hydrazino-5-aminoindazole, 3-hydrazino-5,7-diaminoindazole, 3-hydrazino-4-chloroindazole, 3-hydrazino-5-chloroindazole, 3-hydrazino-6-chloroindazole, 3-hydrazino-5-fluoroindazole, 3-hydrazino-6-bromoindazole, 3-hydrazino-4,7-dichloroindazole, 3-hydrazino-5-trifluoromethylindazole, 3-hydrazino-7-trifluoromethylindazole, 3-hydrazino-7-trifluoromethylindazole, 3-hydrazino-5-trifluoromethyl-7-nitroindazole, 3-hydrazino-5-cyanoindazole, 3-hydrazino-5-cyano-7-3-hydrazino-5-cyanoindazole, 3-hydrazino-5-cyano-7-aminoindazole, 3-hydrazino-5-isopropoxycarbonylindazole, 3-hydrazino-5ethoxycarbonyl-7-ethoxycarbonylaminoindazole and 3-hydrazino-5-trifluoromethyl-7-formylaminoindazole.

The carbonic acid derivatives used as starting materials are similarly known or can be readily prepared by the known method. Pyrocarbonic acid esters include pyrocarbonic acid methyl ester, pyrocarbonic acid ethyl ester, pyrocarbonic acid propyl ester, pyrocarbonic isopropyl ester and pyrocarbonic acid butyl ester; see e.g. Liebigs Ann.Chem. 624, pages 30–36 (1959). Chlorocarbonic acid esters include chlorocarbonic acid methyl ester, chlorocarbonic acid ethyl ester, chlorocarbonic acid propyl ester, chlorocarbonic acid isopropyl ester and chlorocarbonic acid butyl ester; see e.g. Beilsteins Handbuch der Organischen Chemie, edition IV, 3rd supplement, volume 3, pages 23–26.

Diluents optionally can be used and include all organic solvents which are inert towards the particular reactants. These include aliphatic alcohols such as methanol, ethanol, isopropanol or butanol; hydrocarbons such as benzene, toluene and xylene; halohydrocarbons such as chloroform, carbon tetrachloride, chlorobenzene and dichlorobenzenes; carboxylic acid esters such as ethyl acetate; nitriles such as acetonitrile and propionitrile; ketones such as acetone and methyl isobutyl ketone; ethers such as tetrahydrofuran or dioxane; carboxylic acid amides such as dimethylformamide or dimethylacetamide; and heterocyclic bases such as pyridine, picolines, lutidines, collidines, quinoline or isoquinoline, as well as mixtures of these solvents. When pyrocarbonic acid esters are employed, one can utilize an excess which serves as both solvent and reactant. Suitably 100 to 1,000 ml of the diluent are employed per mol of the 3-hydrazinoindazoles of Formula II.

The reaction can be carried out under elevated pressure but in general, it is carried out under normal pressure. The starting materials as a rule dissolve entirely or partially in the reaction mixture while the end products generally crystallize. Separation of the products can be accelerated by cooling and/or by adding such precipitants as ethers, for example diethyl ether or dibutyl ether, or aliphatic hydrocarbons, for example petroleum ether, light benzene or ligroin, or halohydrocarbons, for example carbon tetrachloride. The reaction temperatures can be varied within a substantial range and in general, temperatures between $-10°$ and $+100°$ C, preferably between $-5°$ and $75°$ C, especially between $0°$ and $50°$ C, are used.

Acid binding agents can be used and include inorganic bases such as alkali metal hydroxide, for example calcium hydroxide or barium hydroxide, alkali metal carbonates or alkaline earth metal carbonates such as sodium carbonate, potassium carbonate, calcium carbonate or sodium bicarbonate, amides such as sodamide, and organic bases such as tertiary amines, for example triethylamine, N,N-dimethylaniline, pyridines, quinolines and isoquinolines. The use of pyridines, lutidines and collidines or quinoline as the acid binding agent is particularly advantageous since these can also serve as the diluent or solvent.

The following may be mentioned individually as new active compounds: 3-methoxycarbonylhydrazinoindazole, 3-ethoxycarbonylhydrazinoindazole, 3-isopropoxycarbonylhydrazino-4-methylindazole, 3-ethoxycarbonhyhydrazino-6-ethylindazole, 3-tert-butoxycarbonylhydrazino-5,6-dimethylindazole, 3-ethoxycarbonylhydrazino-5-methoxyindazole, 3-methoxycarbonylhydrazino-7-ethoxyindazole, 3-ethoxycarbonylhydrazino-5,6-bismethoxyindazole, 3-isobutoxycarbonylhydrazino-5-nitroindazole, 3-n-propoxycarbonylhydrazino-5-aminoindazole, 3-methoxycarbonylhydrazino-5-diethylaminoindazole, 3-methoxycarbonylhydrazino-5-pivaloylaminoindazole, 3-ethoxycarbonylhydrazino-5,7-diaminoindazole, 3-n-butoxycarbonylhydrazino-5-chloroindazole, 3-ethoxycarbonylhydrazino-6-chloroindazole, 3-methoxycarbonylhydrazino-6-chloroindazole, 3-n-butoxycarbonylhydrazino-7-chloroindazole, 3-ethoxycarbonylhydrazino-4,7-dichloroindazole, 3-ethoxycarbonylhydrazino-4-trifluoromethylindazole, 3-n-propoxycarbonylhydrazino-5-trifluoromethylindazole, 3-methoxycarbonylhydrazino-6-trifluoromethylindazole, 3-ethoxycarbonylhydrazino-5-fluoroindazole, 3-ethoxycarbonylhydrazino-6-bromoindazole, 3-isobutoxycarbonylhydrazino-5-trifluoromethyl-7-nitroindazole, 3-methoxycarbonylhydrazino-5-trifluoromethyl-7-methoxycarbonylaminoindazole, 3-ethoxycarbonylhydrazino-5-cyanoindazole, 3-ethoxycarbonylhydrazino-5-cyano-7-acetylaminoindazole, 3-ethoxycarbonylhydrazino-5-ethoxycarbonylindazole, 3-ethoxycarbonylhydrazino-6-chloro-7dimethylaminoindazole and 3-n-propoxycarbonylhydrazino-6-chloro-7-formylaminoindazole.

As indicated, the present invention also pertains to the physiologically acceptable salts of the foregoing compounds with alkali metals, alkaline earth metals, ammonia and organic amines as, for example, the sodium salt, the potassium salt, the calcium salt, and the salts with amines such as ethylamine, triethylamine, ethanolamine, diethylaminoethanol, ethylenediamine, piperidine, morpholine, 2-piperidinoethanol, benzylamine, procaine and the like.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In the case of parenteral application a fact which has proved particularly advantageous is that the compounds according to the invention form readily water-soluble salts. These salts are obtained when the compounds according to the invention, in a suitable solvent, are combined with the equimolar amount of a nontoxic inorganic or organic base, as described above. Particularly preferred bases for this purpose are sodium hydroxide, potassium hydroxide, ethanolamine, diethanolamine, triethanolamine, amino-tris-hydroxymethylmethane, glucosamine and N-methyl-glucosamine. Such salts can also be of importance for oral admiminstration in that they accelerate or delay the resorption, as desired. In addition to the salts above, the magnesium, aluminium and iron salts are also useful.

The present invention thus includes pharmaceutical compositions comprising a compound of Formula IA or IB in combination with a pharmaceutical carrier. The amount of the compound present in the composition is at least that calculated to be sufficient upon single or multiple administration to a human or other warm blooded animal to achieve an analgesic, anti-inflammatory or antipyretic effect. The method of achieving such effects in the human or other warm blooded animal through administration is also within the scope of the present invention.

In general, a suitable effect is observed in the case of parenteral administration at daily doses of from about 0.01 to about 50 mg/kg, preferably about 0.1 to about 10 mg/kg, of body weight. In the case of oral administration, the daily dosage is about 0.1 to about 500 mg/kg, preferably about 0.5 to about 100 mg/kg, of body weight. Nevertheless, at times it can be necessary to deviate from these ranges and in particular to do so as a function of the body weight, the nature of the administration route, the species, response, the nature of the formulation, and the time or interval of administration. In some cases less than the above mentioned minimum amount while in others the upper limit must be exceeded. Where large amounts are administered it is advisable to divide these into several individual administrations over the course of the day.

The pharmacological properties can be conveniently observed in recognized in vivo models.

Analgesic action can be observed in the tail flick test on rats in which the tail of male rats is irradiated with a focused heat ray. In this test, untreated animals react after an average irradiation time of $5.1 \pm 0.8$ seconds (reaction time) by drawing away the tail flick. Under the influence of analgesically active compounds, this reaction time becomes longer. Active compounds which after administration prolong the reaction time of the animals to at least 20 seconds are considered to be analgesically active. Five animals are employed per dose. The $ED_{50}$ is the dose which on average lengthens the reaction time of 50% of the animals employed to at least 20 seconds [see generally Wolff et al., J. Clin. Invest., 19, 659–680 (1940)].

Analgesic activity can also be observed in the phenylquinone writhing test in which 100 $\mu$g of phenylquinone, dissolved in 0.5 ml of 5% alcohol, are injected intraperitoneally into rats. A few minutes after administration, the animals show the characteristic writhing reaction, which consists of the animals showing extreme backward extension of the hind paws, flexing the back and lifting the tail. At the same time, wave-like contractions frequently pass over the abdominal muscles. The inhibition of this writhing syndrome is assessed to be an analgesic effect. The substance to be investigated is administered 30 minutes (in the case of subcutaneous administration) or 60 minutes (in the case of oral administration) before the injection of phenylquinone. Five animals are employed per compound and per dose. The $ED_{50}$ is the dose at which the number of writhing reactions in the animals employed is on average reduced to half that of the control group [see generally: Siegmumg et al., Proc. Soc. exp. Biol. Med. 95, 729–731 (1957)].

The anti-inflammatory (antiphlogistic and antiedematous) action of the compounds can be conveniently observed by the inhibition of carrageenin edema on the paw of rats. In this test, a reference measurement on the normal paws of rats is carried out half an hour before and half an hour after oral administration of the test compound, using an antiphlogmeter. One hour after administration of the substance, the edema is started by injecting a carrageein solution into the planta pedis of one hind paw at 2½ hours and 3 hours after the carrageenin injection, the effect on the edematous paw is measured. The relative paw volume is expressed as a percentage of the reference measurement (=100%). The ED₅₀ is the dose at which, in 50% of the animals employed per dose, the difference between the relative paw volume of the treated animals and the relative paw volume of the 10 control groups is 100. Antipyretic action can be observed in rats to which a brewers yeast suspension has been administered subcutaneously. The body temperture is measured rectally before and 16 hours after administration of the beer years. The substance to be tested is administered orally to groups of 5 rats in which the body temperature has risen by at least 1° C. Thereafter, the temperature decrease is measured rectally with a decrease in the body temperature of at least 1° C being assessed as an antipyretic effect. The Ed₅₀ is the dose at which, in 50% of the animals the raised body temperature is lowered by 1° C upon administration of the active substance according to the invention.

The following examples will serve to further typify the nature of this invention without constituting a limitation on the scope thereof. The structure of the reaction products in these examples was confirmed by elementary analysis and by physico-chemical methods of investigation, especially nuclear magnetic resonance, IR-spectroscopy and UV-spectroscopy.

Starting materials are known or were prepared by conventional methods which can be summarized as follows:

0.4 mol of 3-amino-6-chloroindazole is suspended in 500 ml of concentrated hydrochloric acid. A solution of 0.4 mol of sodium nitrite in 60 ml of water is run in at 0°-5° C, while stirring for 2 hours. Then a solution of 0.88 mol of tin-(II)-chloride in 300 ml concentrated hydrochloric acid is added dropwise. Stirring is continued for 5 hours at 0° C, the batch is allowed to stand for 12-15 hours at room temperature and the reaction product which has formed is filtered off and stirred into ice water. Sufficient concentrated sodium hydroxide solution is allowed to run in, while continuing to add ice and stirring vigorously, to bring the pH value to about 11. The colorless, crystalline 3-hydrazino-6-chlorindazole is filtered off and washed with warm water until neutral. Yield, 80% of theory, melting point 160°-162° C (decomposition).

EXAMPLE 1

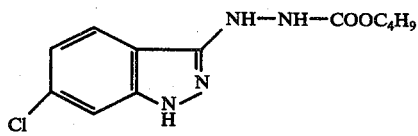

0.04 mol of chlorocarbonic acid n-butyl ester is added dropwise at 0° - 5° C, while stirring, to 0.04 mol of 3-hydrazino-6-chloro-indazole in 20 ml of pyridine. The reaction mixture is stirred for 3 hours at room temperature and then poured into ice water, and the colorless crystals which have precipitated are isolated by filtration. 3-n-Butoxycarbonylhydrazino-6-chloroindazole is obtained. After recrystallisation from a mixture of ligroin and ethanol (9 : 1), the melting point is 150° - 152° C. (Yield, 78% of theory).

EXAMPLE 2

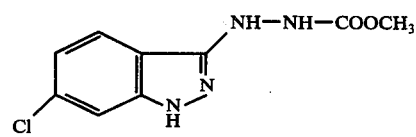

Analogously to Example 1, 0.04 mol of 3-hydrazino-6-chloro-indazole and 0.044 mol of chlorocarbonic acid methyl ester in 25 ml of pyridine at 0° - 5° C, followed by 2 hours at room temperature, give 3-methoxycarbonylhydrazino-6-chloroindazole (melting point 223°-224° C after recrystallisation from methanol: yield, 73% of theory).

EXAMPLE 3

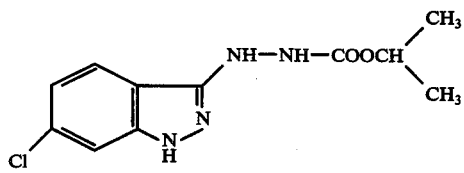

Analogously to Example 1, 0.05 mol of 3-hydrazino-6-chloro-indazole and 0.05 mol of chlorocarbonic acid isopropyl ester in 30 ml of pyridine at 0° - 5° C, followed by 3 hours at room temperature, give 3-isopropoxycarbonylhydrazino-6-chloroindazole (melting point 184° - 185° C after recrystallisation from isopropanol: yield, 68% of theory).

EXAMPLE 4

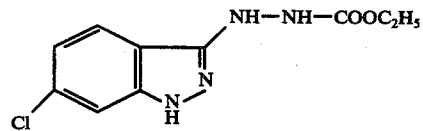

0.1 mol of 3-hydrazino-6-chloro-indazole is introduced into 100 ml of pyrocarbonic acid diethyl ester, in the course of which the temperature rises to 45° C. Stirring of the reaction mixture is continued at room temperature until the evolution of CO₂ has ended, 200 ml of diethyl ether are then run in, the mixture is cooled to 0° C and the colorless crystals which have precipitated are isolated by filtration. 3-Ethoxycarbonylhydrazino-6-chloroindazole is obtained. After recrystallisation from ethanol, the melting point is 210° - 211° C (yield, 71% of theory).

What is claimed is:

1. A compound selected from the group consisting of a 3-carbo(lower alkoxy)hydrazinoindazole of the formula:

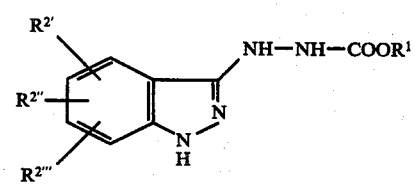

wherein $R^1$ is lower alkyl; and each of $R^{2'}$, $R^{2''}$ and $R^{2'''}$ is selected, independently of the others, from the group consisting of hydrogen, lower alkyl of 1 to 6 carbon atoms, lower alkoxy of 1 to 6 carbon atoms, nitro, amino, lower alkylamino of 1 to 6 carbon atoms, di(lower alkyl of 1 to 6 carbon atoms)amino, lower alkanoylamino of 1 to 6 carbon atoms, carbo(lower alkoxy of 1 to 6 carbon atoms)amino, halo, trifluoromethyl, cyano and carbo(lower alkoxy of 1 to 6 carbon atoms),
and the pharmaceutically acceptable nontoxic salts thereof.

2. A compound according to claim 1 wherein each of $R^{2'}$, $R^{2''}$ and $R^{2'''}$ is selected, independently of the others, from the group consisting of hydrogen, chloro, trifluoromethyl, nitro, amino, cyano, lower alkyl of 1 to 6 carbon atoms or carbo(lower alkoxy of 1 to 6 carbon atoms)amino.

3. A compound according to claim 2 wherein each of $R^{2'}$ and $R^{2'''}$ is hydrogen and $R^{2''}$ is chloro or trifluoromethyl.

4. A compound according to claim 3 wherein $R^{2''}$ is chloro or trifluoromethyl in the 5- or 6-position of the indazole ring.

5. A compound according to claim 4 wherein $R^{2''}$ is chloro in the 6-position.

6. A compound according to claim 1 wherein $R^1$ is methyl, ethyl, propyl, isopropyl or butyl.

7. The compound according to claim 1 which is 3-n-butoxycarbonylhydrazino-6-chloroindazole.

8. The compound according to claim 1 which is 3-isopropoxycarbonylhydrazino-6-chloroindazole.

9. The compound according to claim 1 which is 3-ethoxycarbonylhydrazino-6-chloroindazole.

10. The compound according to claim 1 which is 3-methoxycarbonylhydrazino-6-chloroindazole.

11. The method of achieving an analgesic, anti-inflammatory and/or anti-pyretic effect in humans and other warm blooded animals in need thereof which comprises administering thereto an analgesic, anti-inflammatory and/or anti-pyretic effective amount of a compound according to claim 1.

12. An analgesic, anti-inflammatory and/or anti-pyretic composition comprising a quantity of a compound according to claim 1 sufficient upon administration to a human or other warm blooded animals to achieve analgesic, anti-inflammatory or anti-pyretic effect, in combination with a pharmaceutical carrier.

* * * * *